United States Patent
Bi et al.

(10) Patent No.: US 12,054,398 B2
(45) Date of Patent: Aug. 6, 2024

(54) COPPER ION-DOPED CARBON DOTS, PREPARATION METHOD AND APPLICATION THEREOF AS PHOTOSENSITIZER FOR PHOTODYNAMIC THERAPY

(71) Applicant: ANHUI UNIVERSITY, He Fei (CN)

(72) Inventors: Hong Bi, He Fei (CN); Mingsheng Xu, He Fei (CN); Jingmin Wang, He Fei (CN); Antonio Claudio Tedesco, He Fei (CN)

(73) Assignee: ANHUI UNIVERSITY, Hefei (CN)

( * ) Notice: Subject to any disclaimer, the term of this patent is extended or adjusted under 35 U.S.C. 154(b) by 701 days.

(21) Appl. No.: 17/277,298

(22) PCT Filed: Mar. 15, 2019

(86) PCT No.: PCT/CN2019/078209
§ 371 (c)(1),
(2) Date: Mar. 18, 2021

(87) PCT Pub. No.: WO2020/172917
PCT Pub. Date: Sep. 3, 2020

(65) Prior Publication Data
US 2022/0033266 A1    Feb. 3, 2022

(30) Foreign Application Priority Data
Feb. 28, 2019   (CN) ............................ 201910149157

(51) Int. Cl.
*A61K 41/00*   (2020.01)
*A61P 17/00*   (2006.01)
(Continued)

(52) U.S. Cl.
CPC ........ *C01B 32/914* (2017.08); *A61K 41/0057* (2013.01); *A61P 17/00* (2018.01); *A61P 27/02* (2018.01); *A61P 35/00* (2018.01)

(58) Field of Classification Search
None
See application file for complete search history.

(56) References Cited

FOREIGN PATENT DOCUMENTS

| CN | 104759283 A | * | 7/2015 |
| CN | 105018081 A | * | 11/2015 |

(Continued)

OTHER PUBLICATIONS

English translation of CN-105018081-A Description (Year: 2015).*
(Continued)

*Primary Examiner* — Samir Shah
*Assistant Examiner* — Zachary John Baum
(74) *Attorney, Agent, or Firm* — Bayramoglu Law Offices LLC

(57) ABSTRACT

Copper ion-doped carbon dots (Cu-CDs) and a preparation method thereof are disclosed. The preparation method includes the following steps: using copper nitrate as a dopant to generate a complex of polyacrylic acid and copper ions as a precursor by an in situ polymerization; standing overnight, and performing repeated suction filtration to collect filter residues; then, performing pyrolysis and carbonization to generate carbonized products, dispersing in ultrapure water, taking a supernatant, and then performing extraction and purification to obtain the CDs. When the Cu-CDs prepared by the present invention are used in photodynamic therapy, photothermal/photodynamic synergistic therapy is not required, and the Cu-CDs are suitable for the therapeutic process of skin cancer, lung cancer, pancreatic cancer, esophageal cancer, brain glioma, as well as some skin diseases and ophthalmological diseases.

13 Claims, 3 Drawing Sheets

(51) Int. Cl.
    *A61P 27/02*     (2006.01)
    *A61P 35/00*     (2006.01)
    *C01B 32/914*     (2017.01)

(56) References Cited

FOREIGN PATENT DOCUMENTS

| | | | | |
|---|---|---|---|---|
| CN | 105928914 A | | 9/2016 | |
| CN | 108128767 A | * | 6/2018 | ............. B82Y 20/00 |
| CN | 108165268 A | | 6/2018 | |
| CN | 108786787 A | | 11/2018 | |
| CN | 108822838 A | | 11/2018 | |
| CN | 109370576 A | * | 2/2019 | ............. B82Y 20/00 |
| RU | 2611011 C1 | * | 2/2017 | |
| WO | WO-2009139939 A2 | * | 11/2009 | ........... A61K 31/555 |

OTHER PUBLICATIONS

English translation of CN-108128767-A Description (Year: 2018).*
English translation of CN-109370576-A Description (Year: 2019).*
English translation of CN-104759283-A Description (Year: 2015).*
English translation of RU-2611011-C1 Description (Year: 2017).*
Xiao-Lu Guo, et al., A novel strategy of transition-metal doping to engineer absorption of carbon dots for near-infrared photothermal/photodynamic therapies, Carbon, 2018, pp. 519-530, vol. 134, Elsevier.

* cited by examiner

COPPER ION-DOPED CARBON DOTS, PREPARATION METHOD AND APPLICATION THEREOF AS PHOTOSENSITIZER FOR PHOTODYNAMIC THERAPY

CROSS REFERENCE TO THE RELATED APPLICATIONS

This application is the national phase entry of International Application No. PCT/CN2019/078209, filed on Mar. 15, 2019, which is based upon and claims priority to Chinese Patent Application No. 201910149157.3, filed on Feb. 28, 2019, the entire contents of which are incorporated herein by reference.

TECHNICAL FIELD

The present invention relates to copper ion-doped carbon dots, a preparation method and an application thereof as a photosensitizer for photodynamic therapy, and belongs to the technical field of biomedical materials.

BACKGROUND

Carbon dots (CDs) are a new type of carbon nanomaterials with sizes below 10 nm. CDs have excellent properties such as high fluorescence quantum yield, good photostability, resistance to photobleaching, extremely low toxicity and easy functionalization. The aforementioned properties exemplify the broad application prospects in the fields of biology and medical research, and can be applied to the fields of biological analysis and detection, bioimaging, cancer treatment, and nanomedicine.

Photodynamic therapy (PDT) is a novel method of using laser to activate photosensitive drugs to treat tumors and other diseases. For example, irradiating the tumor site with a specific wavelength can activate the photosensitive drugs that selectively accumulate in the tumor tissue, thereby triggering a photochemical reaction to generate singlet oxygen and kill cancer cells. Photodynamic therapy has been used to treat a variety of diseases such as tumors, skin diseases, ophthalmological diseases, and acne. Compared with traditional tumor therapy, the advantage of photodynamic therapy is that it can treat diseases accurately and effectively with minimal side effects.

At present, the laser used in photodynamic therapy does not penetrate deeply into the tissue, and the intracavitary and deep tumors need to be irradiated by introducing optical fibers into the lesion site, which is quite difficult to operate. When the tumor is large in size, array multipoint irradiation is required, which is cumbersome. Moreover, it is necessary to avoid strong light irradiation for a long time after treatment, and local reactive edema may occur within several days. In addition, this method is not suitable for patients with photosensitizer allergy or deep tumors where optical fibers cannot reach.

The currently reported copper-nitrogen co-doped carbon dots (Guo, Xiao-Lu, et al. "A novel strategy of transition-metal doping to engineer absorption of CDs for near-infrared photothermal/photodynamic therapies." Carbon 134 (2018): 519-530) were synthesized by the reaction of disodium ethylenediaminetetraacetic acid and copper chloride. The obtained CDs are not only doped with copper ions and nitrogen atoms, but also contain metal sodium ions. Moreover, the CDs require photothermal and photodynamic synergistic therapies to produce effects, so the operation process is complicated and cumbersome, which is not conducive to practical applications. Additionally, the singlet oxygen quantum yield of CDs is not high during this process, and the single photodynamic therapy is poor.

SUMMARY

In view of the above-mentioned problems in the prior art, the present invention provides copper ion-doped carbon dots, which have high efficiency in generating singlet oxygen, stable structure, and have better effect for photodynamic therapy.

The present invention further provides a preparation method of the copper ion-doped carbon dots (Cu-CDs) and an application thereof as a photosensitizer for photodynamic therapy.

In order to achieve the above objectives, the present invention adopts a preparation method of Cu-CDs, using copper nitrate as a dopant to generate a complex of polyacrylic acid and copper ions as a precursor by an in situ polymerization; then, performing pyrolysis and carbonization to generate carbonized products, and then performing extraction and purification to obtain the CDs.

As an improvement, the preparation method of the Cu-CDs specifically includes the following steps:
1) weighing and adding 0.3 mol·L$^{-1}$ acrylic acid, a 0.2 mol·L$^{-1}$ copper nitrate solution, ammonium persulfate and hydrazine hydrate to a beaker for a reaction for a predetermined time to obtain a solution, and standing the solution overnight;
2) subjecting the solution obtained above to a suction filtration, collecting and dispersing a filter residue in a predetermined amount of ultrapure water, then performing a suction filtration, collecting a filter residue for a vacuum drying at a predetermined temperature, and collecting powder A;
3) spreading the powder A of step 2) in a crucible, putting the crucible in a muffle furnace for pyrolysis in an air atmosphere, taking out carbonized powder in the crucible, grinding the carbonized powder in a mortar, then performing an ultrasonic treatment for several times to disperse ground carbonized powder in a predetermined amount of ultrapure water, and then standing for subsequently use; then, performing a suction filtration, pouring out a supernatant, and then putting the supernatant into a dialysis bag with a predetermined molecular weight cut-off (MWCO) for dialysis in ultrapure water, and performing a freeze-drying to obtain yellow-brown CDs.

As an improvement, in the step 1), 10-20 mL of the acrylic acid, 2-10 mL of the copper nitrate solution, 10-30 mL of the ammonium persulfate and 5-10 mL of the hydrazine hydrate are added, and a time for the reaction is 25-40 min.

As an improvement, a temperature range of the vacuum drying in the step 2) is 30° C.-45° C.

As an improvement, in the step 3), a heating rate is 2-10° C./min, a temperature for the pyrolysis is 300° C.-500° C., and a time for the pyrolysis is 1.5-2 h.

As an improvement, an organic aqueous microporous filter membrane with a pore diameter of 0.22 μm is used for the suction filtration in the step 2) and step 3).

As an improvement, in the step 3), the molecular weight cut-off of the dialysis bag is 500-1000, a time for the dialysis is 48-72 h and a time for the freeze-drying is 56-72 h, and finally the yellow-brown CDs are obtained.

In addition, the present invention further provides the Cu-CDs obtained by the preparation method.

Finally, the present invention further provides an application of the Cu-CDs prepared by the above preparation method as a photosensitizer for photodynamic therapy.

Compared with the prior art, the present invention has the advantages as follows.

1) The Cu-CDs prepared by the present invention are not only easily dispersed in organic solvents such as absolute ethanol, N,N-dimethylformamide and dichloromethane, but also can be well dispersed in water and phosphate buffer solution (PBS), biological culture medium and other aqueous solution systems.

2) The Cu-CDs prepared by the present invention have a small average particle size, have abundant oxygen and nitrogen-containing functional groups on the surface, and can be well dispersed in organic solvents such as ethanol, which are easy to carry out surface passivation or modification.

3) When the Cu-CDs prepared by the invention are irradiated with visible light and near-infrared wavelength light, singlet oxygen can be produced, and the singlet oxygen quantum yield is as high as 0.86. Compared with Rose Bengal, the ideal photosensitizer currently used for photodynamic therapy with a singlet oxygen quantum yield of 0.75. Based on this, the Cu-CDs of the present invention can be effectively used preparing photodynamic therapy preparations, especially photosensitizers.

4) When the Cu-CDs prepared by the present invention are used in photodynamic therapy, the operation process is simple, which is beneficial to practical application, and the photothermal/photodynamic synergistic therapy is not required.

DETAILED DESCRIPTION OF THE EMBODIMENTS

The following embodiments are further descriptions of the content of the present invention as an explanation of the technical content of the present invention, but the essential content of the present invention is not limited to the following embodiments. Those of ordinary skill in the art can and should know that any simple variations or substitutions based on the essential spirit of the present invention should fall within the protective scope of the present invention.

Embodiment 1

A preparation method of Cu-CDs for photodynamic therapy, specifically includes the steps as follows.

1) 15 mL of 0.3 mol·$L^{-1}$ acrylic acid, a 5 mL of 0.2 mol·$L^{-1}$ copper nitrate solution, 20 mL of ammonium persulfate and 10 mL of hydrazine hydrate are weighed and added to a beaker. After 30 min of a reaction, the solution is left to stand overnight.

2) The solution obtained above is vacuum filtered with an organic microporous filter membrane with a pore diameter of 0.22 μm a filter residue is collected, dispersed in 20 mL of ultrapure water, then vacuum filtered with an organic microporous filter membrane with a pore diameter of 0.22 μm, and then a filter residue is collected, and the operation is repeated for 5 times, and the collected filter residue is vacuum dried at 35° C., and powder A is finally collected.

3) The powder A of step 2) is spread in a crucible, and the crucible is put into a muffle furnace for pyrolysis in an air atmosphere. A heating rate is 10° C.·$min^{-1}$, a temperature for the pyrolysis is 400° C., and a time for the pyrolysis is 2 h. Subsequently, the carbonized powder in the crucible is taken out, ground in a mortar and then dispersed in 20 mL of ultrapure water by an ultrasonic treatment for several times, and then left to stand still. Subsequently, vacuum filtration is carried out with an aqueous microporous filter membrane with a pore diameter of 0.22 μm, the supernatant is poured out, and the operation is repeated for 5 times, and then put into a dialysis bag with a molecular weight cut-off of 500-1000 for dialysis in ultrapure water for 72 h, and freeze-dried for 72 h to obtain yellow-brown CDs.

Figure 1:
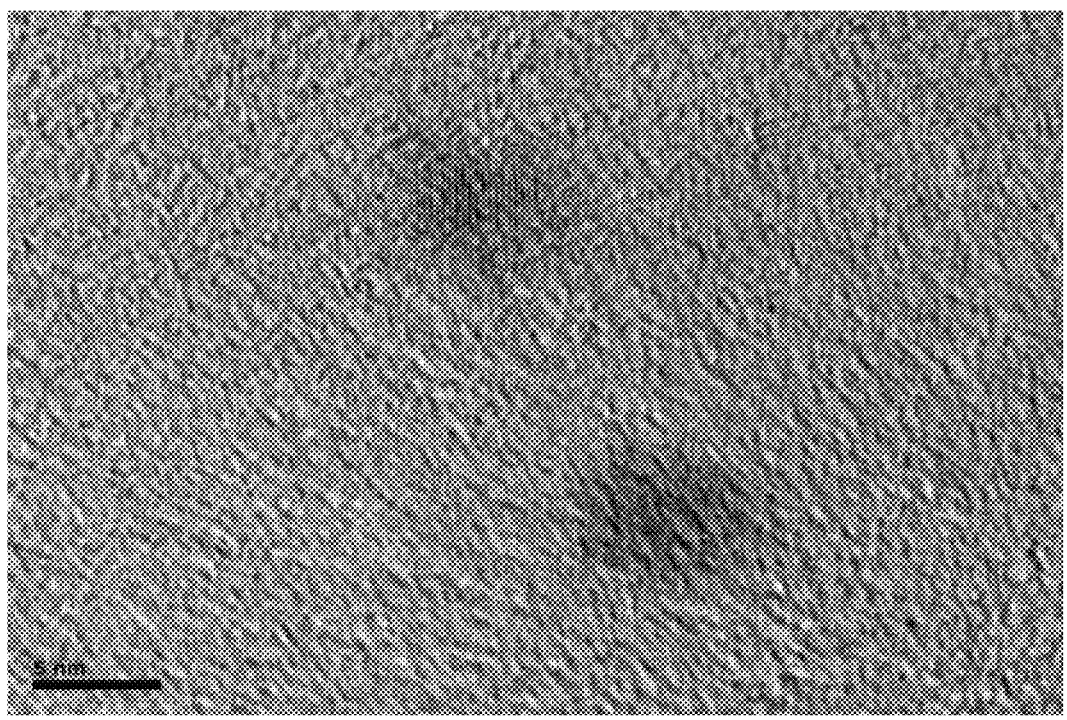
FIG. 1 is a high-resolution transmission electron microscope (HRTEM) image of Cu-CDs of the present invention.

The high-resolution transmission electron micrograph of the prepared Cu-CDs is shown in FIG. 1. It can be seen from the figure that the CDs have a spherical structure with a size of about 5 nm, and there are obvious lattice diffraction fringes inside, indicating that the CDs have good crystallinity.

Figure 2:
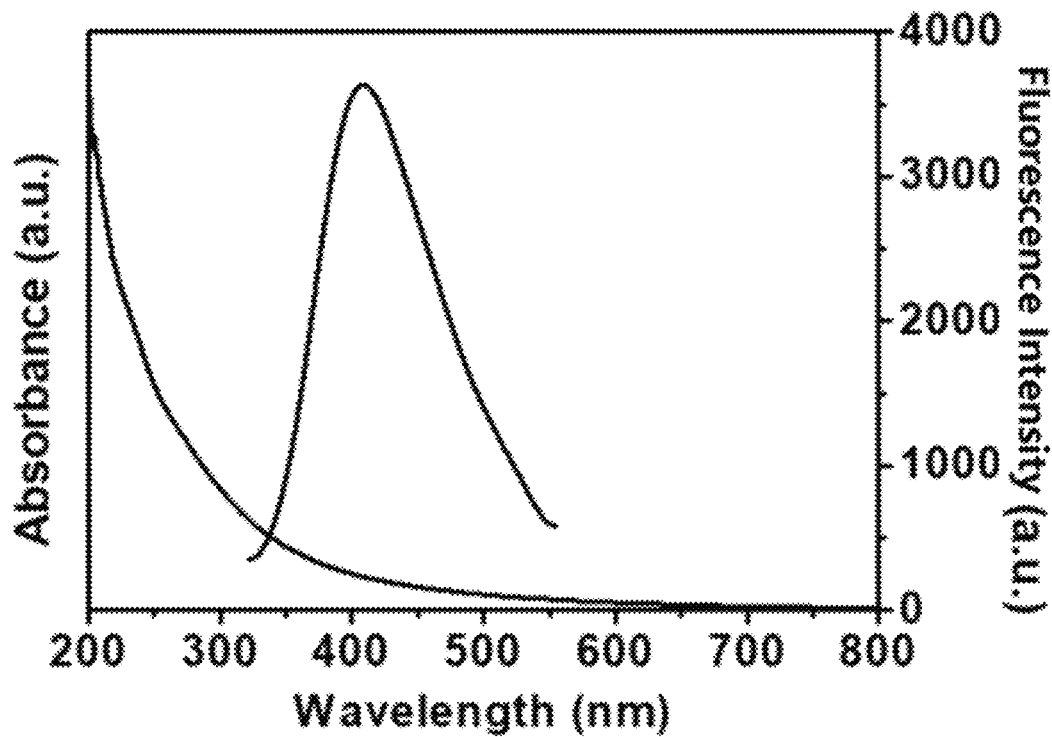
FIG. 2 is a diagram showing ultraviolet-visible absorption spectrum and fluorescence emission spectrum (with an excitation wavelength of 330 nm) of the Cu-CDs of the present invention in ultrapure water.

In addition, FIG. 2 shows the ultraviolet-visible absorption spectrum and fluorescence emission spectrum (with an excitation wavelength of 330 nm) of the Cu-CDs prepared by the present invention in ultrapure water. The analysis shows that under the UV lamp of 365 nm, the aqueous solution of Cu-CDs presents bright green fluorescence; under the excitation of 330 nm light, the aqueous solution of Cu-CDs has a fluorescence emission peak at 420 nm.

Finally, the singlet oxygen produced by the prepared Cu-CDs in the aqueous solution is detected, and the steps are as follows.

(a) 0.0200 g of prepared Cu-CDs are weighed and dissolved in 1 mL of ultrapure water, and then diluted 100 times with ultrapure water to obtain a 0.2 mg·$mL^{-1}$ Cu-CDs solution.

(b) 1 mL of the 0.2 mg·$mL^{-1}$ Cu-CDs solution prepared above is added to 2 mL centrifuge tube A, then 10 μL, of 2,2,6,6-tetramethylpiperidine (TEMP) is added to the centrifuge tube A, and then the centrifuge tube A is irradiated with an LED light (with an excitation wavelength of 300-500 nm) for 10 min.

(c) 30-50 μL of the sample to be tested is extracted by a capillary tube with a diameter of 0.55 mm, then the capillary tube is placed at a bottom of a test tube to adjust the sample to a center of the test tube, and then the test tube is put into an electron paramagnetic resonance (EPR) spectrometer, and the test tube (EPR tube) is placed in a center of the resonant cavity. The EPR measurement parameters are as follows: central magnetic field: 3430.00 Gauss, sweep width: 60.00 Gauss, number of scans: 10, and time constant: 10.49 ms.

Figure 3:
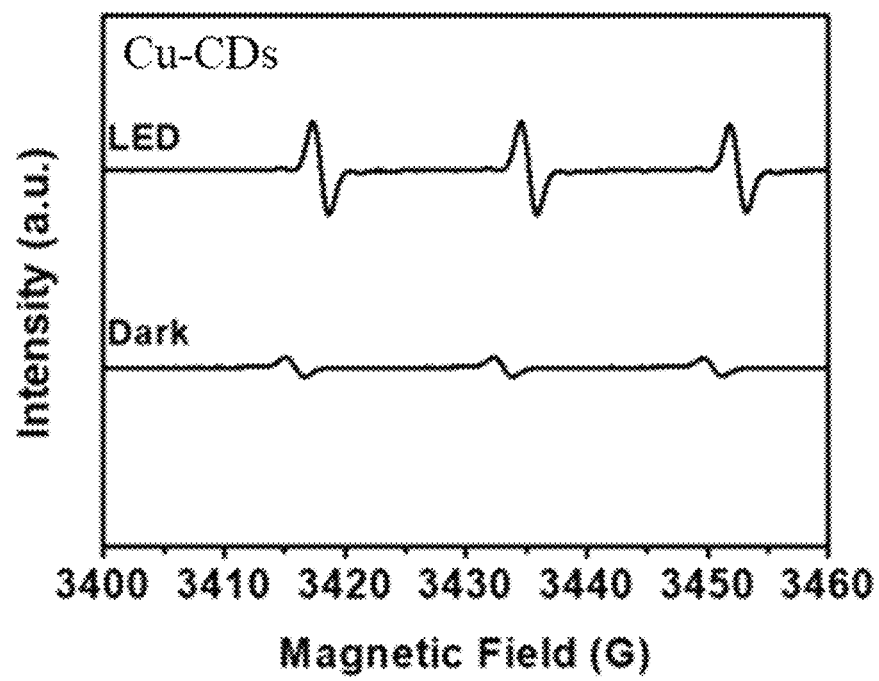
FIG. 3 is a diagram showing electron paramagnetic resonance (EPR) spectra of the Cu-CDs of the present invention using 2,2,6,6-tetramethylpiperidine (TEMP) as a trapping agent under LED laser irradiation and without LED laser irradiation.

(d) In addition, 1 mL of the 0.2 mg·mL$^{-1}$ Cu-CDs solution prepared above is added to 2 mL, centrifuge tube B, then 10 μL of TEMP is added to the centrifuge tube B, and the centrifuge tube B is placed under dark conditions, and then the step (c) is repeated. The results are shown in FIG. 3. It can be seen from FIG. 3 that the Cu-CDs can produce singlet oxygen under the irradiation of LED laser (with an excitation wavelength of 300-500 nm), while only a little or no singlet oxygen is produced under dark conditions.

Embodiment 2

A preparation method of Cu-CDs for photodynamic therapy, specifically includes the steps as follows.

1) 10 mL of 0.3 mol·L$^{-1}$ acrylic acid, a 2 mL of 0.2 mol·L$^{-1}$ copper nitrate solution, 10 mL of ammonium persulfate and 5 mL of hydrazine hydrate are weighed and added to a beaker. After 25 min of a reaction, the solution is left to stand overnight.

2) The solution obtained above is vacuum filtered with an organic microporous filter membrane with a pore diameter of 0.22 μm, a filter residue is collected, dispersed in 20 mL of ultrapure water, then vacuum filtered with an organic microporous filter membrane with a pore diameter of 0.22 μm, and then a filter residue is collected, and the operation is repeated for 5 times, and the collected filter residue is vacuum dried at 30° C., and powder A is finally collected.

3) The powder A of step 2) is spread in a crucible, and the crucible is put into a muffle furnace for pyrolysis in an air atmosphere. A heating rate is 5° C.·min$^{-1}$, a temperature for the pyrolysis is 300° C., and a time for the pyrolysis is 1.5 h. Subsequently, the carbonized powder in the crucible is taken out, ground in a mortar and then dispersed in 20 mL of ultrapure water by an ultrasonic treatment for several times, and then left to stand still. Subsequently, vacuum filtration is carried out with an aqueous microporous filter membrane with a pore diameter of 0.22 μm, the supernatant is poured out, and the operation is repeated for 5 times, and then put into a dialysis bag with a molecular weight cut-off of 500-1000 for dialysis in ultrapure water for 48 h, and freeze-dried for 56 h to obtain yellow-brown CDs.

Embodiment 3

A preparation method of Cu-CDs for photodynamic therapy, specifically includes the steps as follows.

1) 20 mL of 0.3 mol·L$^{-1}$ acrylic acid, a 10 mL of 0.2 mol·L$^{-1}$ copper nitrate solution, 30 mL of ammonium persulfate and 10 mL of hydrazine hydrate are weighed and added to a beaker. After 40 min of a reaction, the solution is left to stand overnight.

2) The solution obtained above is vacuum filtered with an organic microporous filter membrane with a pore diameter of 0.22 μm, a filter residue is collected, dispersed in 20 mL of ultrapure water, then vacuum filtered with an organic microporous filter membrane with a pore diameter of 0.22 μm, and then a filter residue is collected, and the operation is repeated for 5 times, and the collected filter residue is vacuum dried at 45° C., and powder A is finally collected.

3) The powder A of step 2) is spread in a crucible, and the crucible is put into a muffle furnace for pyrolysis in an air atmosphere. A heating rate is 2° C.·min$^{-1}$, a temperature for the pyrolysis is 500° C., and a time for the pyrolysis is 1.5 h. Subsequently, the carbonized powder in the crucible is taken out, ground in a mortar and then dispersed in 20 mL of ultrapure water by an ultrasonic treatment for several times, and then left to stand still. Subsequently, vacuum filtration is carried out with an aqueous microporous filter membrane with a pore diameter of 0.22 μm, the supernatant is poured out, and the operation is repeated for 5 times, and then put into a dialysis bag with a molecular weight cut-off of 500-1000 for dialysis in ultrapure water for 60 h, and freeze-dried for 64 h to obtain yellow-brown CDs.

Embodiment 4

The Cu-CDs prepared by the present invention are used as photosensitizers in photodynamic therapy to increase the amount of singlet oxygen produced under light, to improve the effect of photodynamic therapy. The Cu-CDs can be applied to the treatment process of skin cancer, lung cancer, pancreatic cancer, esophageal cancer, brain glioma, as well as some skin diseases and ophthalmological diseases.

Culture conditions of Hela cells. In a 60 nm cell culture dish, 3 mL of Gibco Dulbecco's modified eagle medium (DMEM) containing 10% fetal bovine serum is added, and then cultured in a constant temperature incubator at 37° C. with 5% $CO_2$. Hela cells are adherent cells. When the cells grow to 80%, the cells are digested with 1 mL of 0.25% a trypsin solution for 2 min, and 1 mL of the culture solution containing 10% fetal bovine serum is used to stop the trypsinization, and the cells at the bottom of the dish are repeatedly pipetted to make them fully dispersed. After centrifugation at 100 rpm for 5 min, the supernatant is discarded, and a fresh medium is added to the cell pellets. After being evenly pipetted, the cell solution is transferred to a new cell culture dish at a ratio of 1:4 to continue culturing for subsequently use.

The MTT method is used to detect the cytotoxicity of the prepared Cu-CDs. The MTT method is commonly used for detecting cell survival and growth. The detection principle is: the succinate dehydrogenase in the mitochondria of living cells can reduce exogenous MTT (thiazole blue) into water-insoluble blue-purple crystalline formazan that deposits in the cells, while dead cells do not have such function; then DMSO (dimethyl sulfoxide) is used to dissolve the formazan in the cells, and then the absorbance is measured at 540 nm or 720 nm with an enzyme-linked immunoassay, which indirectly reflects the cell survival rate.

Figure 4:
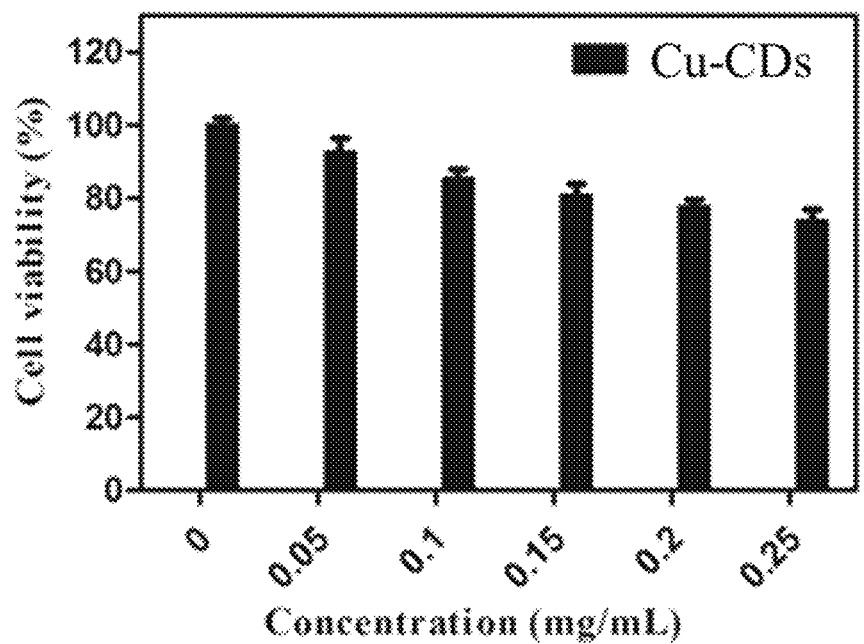
FIG. 4 is a diagram showing the results of a cytotoxicity test by the MTT (3-[4,5-dimethylthiazol-2-yl]-2,5 diphenyl tetrazolium bromide) method after co-cultivating different concentrations of Cu-CDs of the present invention with Hela cells for 24 h.

The results of MIT cytotoxicity test. Hela cells (human cervical cancer cells) are co-cultured with different concentrations of Cu-CDs for 24 h without light. The results are shown in FIG. 4. It can be seen from FIG. 4 that the survival rate of Hela cells is still maintained above 80%, indicating that the prepared Cu-CDs have good biocompatibility.

Figure 5:
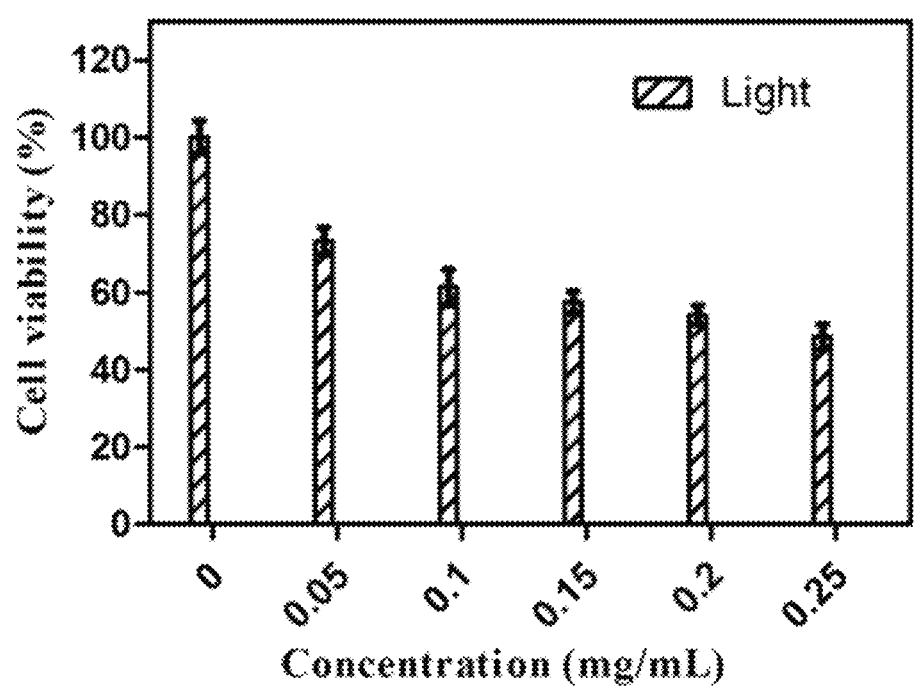
FIG. 5 is a diagram showing the results of a cytotoxicity test by the MTT method after co-cultivating different concentrations of the Cu-CDs of the present invention with the Hela cells for 24 h and then irradiating with light for 10 min.

The results of MTT cytotoxicity test. Hela cells are co-cultured with different concentrations of Cu-CDs for 24 h, and then irradiated with light for 10 min. The results are shown in FIG. 5. As can be seen from FIG. 5, the cytotoxicity of Cu-CDs with different concentrations under light irradiation is significantly greater than that without light under dark conditions. When the concentration of Cu-CDs is 0.25 mg·mL$^{-1}$, the cytotoxicity of Cu-CDs under light irradiation is 1.5 times that of Cu-CDs under dark conditions. The results show that the Cu-CDs have the application value for photodynamic therapy.

The preparation method of the present invention has the advantages of simple reaction step, low cost, being environmentally friendly, and others, and the prepared Cu-CDs has uniform particle size, stable structure and fluorescence property.

The Cu-CDs prepared by the invention can generate singlet oxygen under the irradiation of visible light and near-infrared wavelength light, and are ideal photosensitizers used for photodynamic therapy. The Cu-CDs are suitable for the therapeutic process of skin cancer, lung cancer, pancreatic cancer, esophageal cancer, brain glioma, as well as some skin diseases and ophthalmological diseases, and have a broad application prospect.

The foregoing descriptions are merely preferred embodiments of the present invention, which are not used to limit the present invention. Any modifications, equivalent substitutions, improvements within the spirit and principle of the present invention should fall within the protective scope of the present invention.

What is claimed is:

1. A preparation method of copper ion-doped carbon dots (Cu-CDs), comprising: using copper nitrate as a dopant to generate a complex of polyacrylic acid and copper ions by an in situ polymerization, wherein the complex of polyacrylic acid and copper ions is used as a precursor, standing the precursor overnight, and performing a repeated suction filtration on the precursor to collect filter residues; then performing a pyrolysis and a carbonization on the filter residues to generate a carbonized product, dispersing the carbonized product in water to obtain a mixture, taking a supernatant from the mixture, and then performing an extraction and a purification on the supernatant to obtain the Cu-CDs.

2. The preparation method of the Cu-CDs according to claim 1, comprising the following steps:
   1) weighing and adding 0.3 mol·$L^{-1}$ acrylic acid, a 0.2 mol·$L^{-1}$ copper nitrate solution, ammonium persulfate and hydrazine hydrate to a beaker for a reaction for a predetermined time to obtain a solution, and standing the solution overnight;
   2) subjecting the solution to a first suction filtration, collecting and dispersing a first filter residue in a predetermined amount of the water, then performing a second suction filtration, collecting a second filter residue for a vacuum drying at a predetermined temperature, and collecting a powder;
   3) spreading the powder of step 2) in a crucible, putting the crucible in a muffle furnace for the pyrolysis in an air atmosphere to obtain a carbonized powder, taking out the carbonized powder in the crucible, grinding the carbonized powder in a mortar to obtain a ground carbonized powder, then performing an ultrasonic treatment on the ground carbonized powder for a plurality of times to disperse the ground carbonized powder in a predetermined amount of the water to obtain the mixture, and then standing the mixture for subsequent use; then, performing a third suction filtration on the mixture, pouring out the supernatant from the mixture, and then putting the supernatant into a dialysis bag with a predetermined molecular weight cut-off for a dialysis in the water to obtain a resulting product, and performing a freeze-drying on the resulting product to obtain the Cu-CDs with a yellow-brown color.

3. The preparation method of the Cu-CDs according to claim 2, wherein in the step 1), 10-20 mL of the acrylic acid, 2-10 mL of the copper nitrate solution, 10-30 mL of the ammonium persulfate and 5-10 mL of the hydrazine hydrate are added, and the predetermined time for the reaction is 25-40 min.

4. The preparation method of the Cu-CDs according to claim 2, wherein the predetermined temperature of the vacuum drying in the step 2) is 30° C.-45° C.

5. The preparation method of the Cu-CDs according to claim 2, wherein in the step 3), a heating rate of the pyrolysis is 2-10° C./min, a temperature for the pyrolysis is 300° C.-500° C., and a time for the pyrolysis is 1.5-2 h.

6. The preparation method of the Cu-CDs according to claim 2, wherein an organic aqueous microporous filter membrane with a pore diameter of 0.22 μm is used for the first suction filtration, the second suction filtration and the third suction filtration in the step 2) and step 3).

7. The preparation method of the Cu-CDs according to claim 2, wherein in the step 3), the predetermined molecular weight cut-off of the dialysis bag is 500-1000, a time for the dialysis is 48-72 h and a time for the freeze-drying is 56-72 h.

8. A method of a photodynamic therapy, comprising a step of using copper ion-doped carbon dots (Cu-CDs) as a photosensitizer for the photodynamic therapy, wherein the Cu-CDs are prepared by a preparation method comprising: using copper nitrate as a dopant to generate a complex of polyacrylic acid and copper ions by an in situ polymerization, wherein the complex of polyacrylic acid and copper ions is used as a precursor, standing the precursor overnight, and performing a repeated suction filtration on the precursor to collect filter residues; then performing a pyrolysis and a carbonization on the filter residues to generate a carbonized product, dispersing the carbonized product in water to obtain a mixture, taking a supernatant from the mixture, and then performing an extraction and a purification on the supernatant to obtain the Cu-CDs.

9. The method of a photodynamic therapy according to claim 8, wherein the preparation method comprises the following steps:
   1) weighing and adding 0.3 mol·$L^{-1}$ acrylic acid, a 0.2 mol·$L^{-1}$ copper nitrate solution, ammonium persulfate and hydrazine hydrate to a beaker for a reaction for a predetermined time to obtain a solution, and standing the solution overnight;
   2) Subjecting the solution to a first suction filtration, collecting and dispersing a first filter residue in a predetermined amount of the water, then performing a second suction filtration, collecting a second filter residue for a vacuum drying at a predetermined temperature, and collecting a powder;
   3) Spreading the powder of step 2) in a crucible, putting the crucible in a muffle furnace for the pyrolysis in an air atmosphere to obtain a carbonized powder, taking out the carbonized powder in the crucible, grinding the carbonized powder in a mortar to obtain a ground carbonized powder, then performing an ultrasonic treatment on the ground carbonized powder for a plurality of times to disperse the ground carbonized powder in a predetermined amount of the water to obtain the mixture, and then standing the mixture for subsequently use; then, performing a third suction filtration on the mixture, pouring out the supernatant from the mixture, and then putting the supernatant into a dialysis bag with a predetermined molecular weight cut-off for a dialysis in the water to obtain a resulting product, and performing a freeze-drying on the resulting product to obtain the Cu-CDs with a yellow-brown color.

10. The method of a photodynamic therapy according to claim 9, wherein in the step 1), 10-20 mL of the acrylic acid, 2-10 mL of the copper nitrate solution, 10-30 mL of the ammonium persulfate and 5-10 mL of the hydrazine hydrate are added, and the predetermined time for the reaction is 25-40 min.

11. The method of a photodynamic therapy according to claim 9, wherein the predetermined temperature of the vacuum drying in the step 2) is 30° C.-45° C.

12. The method of a photodynamic therapy according to claim 9, wherein in the step 3), a heating rate of the pyrolysis is 2-10° C./min, a temperature for the pyrolysis is 300° C.-500° C., and a time for the pyrolysis is 1.5-2 h.

13. The method of a photodynamic therapy according to claim 9, wherein an organic aqueous microporous filter membrane with a pore diameter of 0.22 μm is used for the first suction filtration, the second suction filtration and the third suction filtration in the step 2) and step 3).

* * * * *